US011340221B2

(12) United States Patent
Hu et al.

(10) Patent No.: US 11,340,221 B2
(45) Date of Patent: May 24, 2022

(54) USE OF MOLECULAR MARKER DKK-3 ASSOCIATED WITH MUSCLE ATROPHY

(71) Applicant: Shanghai Institutes for Biological Sciences, Chinese Academy of Sciences, Shanghai (CN)

(72) Inventors: Ping Hu, Shanghai (CN); Jie Yin, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 506 days.

(21) Appl. No.: 15/569,981

(22) PCT Filed: Apr. 28, 2016

(86) PCT No.: PCT/CN2016/080441
§ 371 (c)(1),
(2) Date: Feb. 6, 2018

(87) PCT Pub. No.: WO2016/173501
PCT Pub. Date: Nov. 3, 2016

(65) Prior Publication Data
US 2018/0156794 A1   Jun. 7, 2018

(30) Foreign Application Priority Data

Apr. 29, 2015 (CN) .......................... 201510215819.4

(51) Int. Cl.

| | |
|---|---|
| *C12Q 1/6883* | (2018.01) |
| *C12Q 1/6851* | (2018.01) |
| *C12Q 1/6876* | (2018.01) |
| *C12Q 1/6806* | (2018.01) |
| *C12Q 1/686* | (2018.01) |
| *G01N 33/566* | (2006.01) |
| *G01N 33/68* | (2006.01) |
| *C12N 5/077* | (2010.01) |
| *C12Q 1/02* | (2006.01) |
| *G01N 33/50* | (2006.01) |

(52) U.S. Cl.
CPC .......... *G01N 33/566* (2013.01); *C12N 5/0658* (2013.01); *C12Q 1/025* (2013.01); *C12Q 1/686* (2013.01); *C12Q 1/6806* (2013.01); *C12Q 1/6851* (2013.01); *C12Q 1/6876* (2013.01); *C12Q 1/6883* (2013.01); *G01N 33/5061* (2013.01); *G01N 33/68* (2013.01); *G01N 33/6854* (2013.01); *G01N 33/6887* (2013.01); *C12N 2503/02* (2013.01); *C12Q 2600/158* (2013.01)

(58) Field of Classification Search
CPC .. C12Q 1/6851; C12Q 1/6876; C12Q 1/6806; C12Q 1/686; C12Q 2600/158; G01N 33/566; G01N 33/68; G01N 33/5061; G01N 33/6854; G01N 33/6887
See application file for complete search history.

(56) References Cited

U.S. PATENT DOCUMENTS

| | | | | |
|---|---|---|---|---|
| 2002/0110820 A1* | 8/2002 | Ramaswamy | ....... | C12Q 1/6886 435/6.14 |
| 2002/0155480 A1* | 10/2002 | Golub | .............. | G01N 33/57407 435/6.14 |
| 2012/0135882 A1* | 5/2012 | Bottinger | ............. | C12Q 1/6883 506/9 |

FOREIGN PATENT DOCUMENTS

| | | |
|---|---|---|
| CN | 103140760 A | 6/2013 |
| JP | 2006-524034 A | 10/2006 |
| JP | 2008-535790 A | 9/2008 |
| KR | 1020120121754 A | 11/2012 |
| KR | 20140070794 A | 6/2014 |
| WO | WO02066509 A2 | 8/2002 |

OTHER PUBLICATIONS

Ginzinger, D.G. Gene quantification using real-time quantitative PCR: An emerging technology hits the mainstream. Experimental Hematology 2002; 30: 503-512 (Year: 2002).*
Arya et al. Basic principles of real-time quantitative PCR. Expert Review of Molecular Diagnostics 2005; 5: 209-2019 (Year: 2005).*
Wilhelm, J. and Pingoud, A. Real-time polymerase chain reaction. ChemBioChem 2003; 4: 1120-1128 (Year: 2003).*
San Segundo-Val, I. and Sanz-Lozano, C.S. Introduction to the Gene Expression Analysis. Methods in Molecular Biology 2016; 1434: 29-43 (Year: 2016).*
Mizobuchi et al. REIC/Dkk-3 induces cell death in human malignant glioma. Neuro-Oncology 2008; 10: 244-253 (Year: 2008).*
Kuphal et al. Expression of Dickkopf genes is strongly reduced in malignant melanoma. Oncogene 2006; 25: 5027-5036 (Year: 2006).*
Campanaro et al. Gene expression profiling in dysferlinopathies using a dedicated muscle microarray. Human Molecular Genetics 2002; 11: 3283-3298 (Year: 2002).*
Chen et al. Expression Profiling in the Muscular Dystrophies: Identification of Novel Aspects of Molecular Pathophysiology. The Journal of Cell Biology 2000; 151: 1321-1336 (Year: 2000).*
International Search Report dated Aug. 3, 2016 for International Application No. PCT/CN2016/080441, 4 pages.

* cited by examiner

*Primary Examiner* — Angela M. Bertagna
(74) *Attorney, Agent, or Firm* — Lee & Hayes, P.C.

(57) ABSTRACT

Disclosed are a protein molecular marker Dkk-3 protein associated with age-related muscle atrophy and the use thereof in the diagnosis of age-related muscle atrophy. The expression level of the Dkk-3 protein in amyotrophic cells is significantly higher than that in normal myocytes or tissues, and thus the Dkk-3 protein can be used as an effective marker for the detection of age-related muscle atrophy.

10 Claims, 3 Drawing Sheets

Specification includes a Sequence Listing.

USE OF MOLECULAR MARKER DKK-3 ASSOCIATED WITH MUSCLE ATROPHY

CROSS REFERENCE TO RELATED APPLICATIONS

The present application is the U.S. National Phase application of International Application No. PCT/CN2016/080441, filed Apr. 28, 2016, which claims the benefit of Chinese Application No. CN201510215819.4 filed Apr. 29, 2015, both of which are hereby incorporated by reference in their entirety.

REFERENCE TO SEQUENCE LISTING

The Sequence Listing associated with this application is provided in text format in lieu of a paper copy and is hereby incorporated by reference into the specification. The name of the text file containing the Sequence Listing is 5086-0009US_ST25.txt. The text file is 6473 bytes, was created on Jan. 25, 2022, and is being submitted electronically via EFS-Web

TECHNICAL FIELD

The present invention relates to the field of biotechnology, particularly to the screening and use of a protein molecular marker Dkk-3 associated with age-related muscle atrophy.

BACKGROUND ART

The methods now available for diagnosing muscle atrophy mainly include a medical history enquiry, a muscular appearance inspection, an observation for the presence or absence of fasciculation and apparent muscular mass loss in patients, as well as an electromyography analysis combined with nerve conduction velocity and evoked potentials. There has no molecular diagnostic methods yet.

Dkk-3 is a member of the Dickkopf protein family and belongs to the extracellular secreted proteins. However, there has no findings reporting the association between the expression level of Dkk-3 and the occurrence of muscle atrophy.

Therefore, it is of significant importance to study and develop genes and/or proteins that are highly expressed in muscle atrophy for therapeutic and diagnostic purposes. There is an urgent need in the art for genes and/or proteins that are highly expressed in muscle atrophy.

SUMMARY OF THE INVENTION

In order to solve problems in the prior art, an object of the present invention is to provide the screening and use of a protein molecular marker Dkk-3 associated with age-related muscle atrophy.

The present invention is realized by the following technical solutions:

In the first aspect, the present invention provides the use of a Dkk-3 protein, an antibody thereof, an encoding gene thereof or a transcript thereof in the preparation of a reagent for detecting age-related muscle atrophy.

In the second aspect, the present invention provides a method for in vitro determining whether or not the expression level of the Dkk-3 gene in the myocytes or muscle tissues to be tested is abnormal, said method comprising the following steps of:

(1) extracting the mRNA of the myocytes or muscle tissues to be tested and subjecting the mRNA to reverse transcription into cDNA;

(2) obtaining an amplification product of Dkk-3 through amplification by a quantitative PCR method using a primer that specifically amplifies the Dkk-3 transcript and the cDNA in step (1) as a template; and (3) comparing the amount of the Dkk-3 amplification product in the myocytes or muscle tissues to be tested in step (2) with the amount of the Dkk-3 amplification product in normal myocytes or muscle tissues, where the amount of the Dkk-3 amplification product in the myocytes or muscle tissues to be tested is higher than the amount of the Dkk-3 amplification product in normal myocytes or muscle tissues, indicating that the expression level of the Dkk-3 gene in the myocytes or muscle tissues to be tested is abnormal.

The above method may be used for non-disease diagnosis, for example, for the study of the relevant mechanisms only.

In the third aspect, the present invention provides a method for in vitro determining whether or not the expression level of the Dkk-3 protein in the myocytes or muscle tissues to be tested is abnormal, said method comprising the following steps of:

(1) detecting the amount of the Dkk-3 protein in the myocytes or muscle tissues to be tested with specific antibodies against the Dkk-3 protein; and (2) comparing the amount of the Dkk-3 protein in the myocytes or muscle tissues to be tested in step (1) with the amount of the Dkk-3 protein in normal myocytes or muscle tissues, where the amount of the Dkk-3 protein in the myocytes or muscle tissues to be tested is higher than the amount of the Dkk-3 protein in normal myocytes or muscle tissues, indicating that the expression level of the Dkk-3 protein in the myocytes or muscle tissues to be tested is abnormal.

The above method may be used for non-disease diagnosis, for example, for the study of the relevant mechanisms only.

In the fourth aspect, the present invention provides a kit for detecting age-related muscle atrophy, said kit comprising: a primer that specifically amplifies a Dkk-3 transcript and/or a specific antibody against Dkk-3.

In one preferred embodiment of the present invention, the kit further comprises a reagent selected from the group of:

(1) a positive control; and (2) a negative control.

In the fifth aspect, the present invention provides the use of a Dkk-3 protein, an encoding gene thereof or a transcript thereof as a marker for detecting age-related muscle atrophy.

In the sixth aspect, the present invention provides a method for detecting age-related muscle atrophy or susceptibility to age-related muscle atrophy, said method comprising the following steps of:

(1) obtaining an amplification product of Dkk-3 through amplification by a quantitative PCR method using the primer that specifically amplifies the Dkk-3 transcript and the cDNA in the myocytes or muscle tissues of an individual to be tested as a template, and examining whether the amount of formed amplification products is higher than that in a normal control; or under conditions suitable for the formation of antibody complexes, contacting the specific antibodies against the Dkk-3 protein with samples from the individual to be tested, and examining whether the amount of formed antibody complexes is higher than that in a normal control; and (2) if the amount of formed amplification products or antibody complexes is higher than that in a normal control, indicating that the individual has age-related muscle atrophy or has greater susceptibility to age-related muscle atrophy than the normal population.

The above method may be used for non-disease diagnosis, for example, for the study of the relevant mechanisms only.

In the seventh aspect, the present invention provides a method for screening a drug for the treatment of age-related muscle atrophy, said method comprising the following steps of:

(1) preparing a cell line expressing the Dkk-3 protein by loading the cDNA of the Dkk-3 gene into an expression vector and transfecting a mammalian cell line with the expression vector; and (2) adding a test compound into the culture medium of the cell line expressing the Dkk-3 protein in step (1), wherein the test compound that results in the improvement in or cure of age-related muscle atrophy symptoms after administration is a candidate drug for the treatment of age-related muscle atrophy.

The advantageous effects of the present invention lie in:

(1) The present invention reveals for the first time the correlation between Dkk-3 and age-related muscle atrophy, wherein the Dkk-3 is highly expressed in more than 90% of amyotrophic cases with a ratio of Dkk-3 expression in amyotrophic cells to Dkk-3 expression in normal cells >3.0:1. In addition, the present method is significantly superior to the existing diagnostic methods in sensitivity and accuracy regarding detection, which is the first molecular diagnostic method available for detecting age-related muscle atrophy, and is also easy in operation.

(2) The fact that the expression level of muscular Dkk-3 is detected by PCR and other molecular diagnostic methods for aging related muscle atrophy diagnosis makes the diagnosis possible in the early stage of age-related muscle atrophy. Traditional diagnostic methods mainly rely on the observation of muscle morphology combined with a muscle strength test. Only when muscles shrink to a considerable extent, will the muscular morphology and strength change, which makes it impossible to be noticed and intervened in the early stage of age-related muscle atrophy. Furthermore, since the muscle strength test generally detects the contractility of a group of muscles, it lacks sensitivity in the determination of the presence or absence of age-related muscle atrophy in a specific muscle. However, the molecular diagnosis can accurately focus on the sampling position and detect the muscular shrinking in each muscle. Molecular diagnosis makes quantitative detection and standardized detection process possible, and eliminates human subjective error factors in the traditional observation and diagnostic methods. What's more, PCR detection requires very few samples, making it an easy and fast detection.

BRIEF DESCRIPTION OF THE DRAWINGS

FIGS. 4A, 4B, and 4C: The overexpression of Dkk-3 in the myotube of mice cultured in vitro resulted in age-related muscle atrophy.

FIGS. 6A and 6B: The overexpression of Dkk-3 in mouse muscles led to muscle atrophy.

DETAILED DESCRIPTION OF EMBODIMENTS

After an extensive and in-depth research, the present invention has not only managed to clone the human Dkk-3 gene sequence, but also explored the role of Dkk-3 gene in the process of muscle shrinking using various models. Surprisingly, it was found that Dkk-3 is associated with age-related muscle atrophy.

A fragment of DNA sequence was cloned in the cDNA library of the senile muscles by PCR using a pair of primers that were designed with reference to the conserved region of cDNA of the Dkk-3 gene in human muscle. The sequencing results showed that the sequence was 1053 bp in length and had 92% and 93% homology with the corresponding regions of cDNA of Dkk-3 in rats and mice, respectively.

A functional test of the Dkk-3 gene was carried out by experimental models using mice as experimental animals. A virus capable of expressing the Dkk-3 gene was injected intramuscularly. The results showed that the expression of Dkk-3 gene gave rise to increased expression of age-related muscle atrophy-specific genes Atrogin-1 and MuRF-1, thereby leading to age-related muscle atrophy.

In view of the high specific expression of Dkk-3 mRNA in muscle tissues, it suggests that Dkk-3 protein is related to age-related muscle atrophy. Drugs and diagnostic techniques designed according to the human Dkk-3 gene and expression products thereof can be used to diagnose and treat human age-related muscle atrophy.

Definition

"Nucleic acid" as used herein refers to deoxyribonucleotides or ribonucleic acid polymers in a single-stranded or double-stranded form. Unless otherwise stated, the term has included analogs of natural nucleotides that can function in a manner similar to that of natural nucleotides.

"Hybridization" refers to binding two single-stranded nucleic acids by pairing their complementary bases.

"Basically bound to" or "specific binding" or "selective binding" or "specifically hybridized to" refers to a complementary hybridization between oligonucleotides and target sequences, and may include minor mismatches which make it possible to detect the desired target polynucleotide sequence by reducing the stringency of the hybridization medium. The term also means that, under stringent conditions, a molecule binds, complexes or hybridizes to a particular nucleotide sequence. When the particular nucleotide sequence is present in a complex mixture (such as total cellular DNA or RNA), the term "stringent conditions"

refers to conditions under which the probe hybridizes to the target sequence rather than other sequences. The stringent conditions are sequence-dependent and may vary in different situations. Longer sequences can specifically hybridize at higher temperatures. Typically, the selected stringent conditions are about 5° C. lower than the thermal melting point (Tm) of the deduced sequence at defined ionic strength and pH. The Tm is the temperature (under defined ionic strength, pH and nucleic acid concentration) at which approximately 50% of the probes complementary to the target sequence hybridize to the target sequence at equilibrium. In general, for short probes, the stringent conditions are conditions under which the salt concentration is at least about 0.02 mol/L $Na^+$ concentration, 0.0015 mol/L $Mg^{2+}$ (or other salt), pH 7.0-8.3, and a temperature of at least about 60° C. The stringent conditions can also be achieved by the addition of a destabilizing agent such as formamide, DMSO, etc.

It will be understood by those skilled in the art that the exact sequence of the specific primer and probe described herein can be modified to some extent to produce primers or probes that are "substantially identical" to those disclosed herein but retain the basic ability to bind to the target sequence.

Dkk-3 Protein and Gene

Based on the correlation between Dkk-3 and age-related muscle atrophy and the sequence information of Dkk-3 as disclosed in the present invention, one skilled in the art can use conventional techniques in the art to produce a Dkk-3 gene, a protein, or a fragment thereof.

In the present invention, terms "Dkk-3 protein", "Dkk-3 polypeptide", "highly expressed Dkk-3 protein in age-related muscle atrophy" or "the protein of the present invention" and the like are used interchangeably, all referring to the Dkk-3 protein of a human or other mammals (Genbank accession number AAQ88744.1; NCBI accession number AY358378.1).

A particularly preferred Dkk-3 protein is a human Dkk-3 protein whose amino acid sequence is as shown in SEQ ID NO: 1, specifically:

MQRLGATLLCLLLAAAVPTAPAPAPTATSAPVKPGPALSYPQEE

ATLNEMFREVEELMEDTQHKLRSAVEEMEAEEAAAKASSEVNLANLPPSY

HNETNTDT

KVGNNTIHVHREIHKITNNQTGQMVFSETVITSVGDEEGRRSHECIIDED

CGPSMYCQ

FASFQYTCQPCRGQRMLCTRDSECCGDQLCVWGHCTKMATRGSNGTICDN

QRDCQPGL

CCAFQRGLLFPVCTPLPVEGELCHDPASRLLDLITWELEPDGALDRCPCA

SGLLCQPH

SHSLVYVCKPTFVGSRDQDGEILLPREVPDEYEVGSFMEEVRQELEDLER

SLTEEMAL

GEPAAAAAALLGGEEI.

The nucleotide sequence encoding the Dkk-3 protein is as shown in SEQ ID NO: 2, specifically:

atgcagcg gcttggggcc accctgctgtgcctgctgct ggcggcggcg gtccccacgg ccccgcgcc cgctccgacg gcgacctcggctccagtcaa gcccggcccg gctctcagct acccgcagga ggaggccacc ctcaatgagatgttccgcga ggttgaggaa ctgatggagg acacgcagca caaattgcgc agcgcggtggaagagatgga ggcagaagaa gctgctgcta aagcatcatc agaagtgaac ctggcaaacttacctcccag ctatcacaat gagaccaaca cagacacgaa ggttggaaat aataccatccatgtgcaccg agaaattcac aagataacca acaaccagac tggacaaatg gtcttttcagagacagttat cacatctgtg ggagacgaag aaggcagaag gagccacgag tgcatcatcgacgaggactg tgggcccagc atgtactgcc agtttgccag cttccagtac acctgccagccatgccgggg ccagaggatg ctctgcaccc gggacagtga gtgctgtgga gaccagctgtgtgtctgggg tcactgcacc aaaatggcca ccaggggcag caatgggacc atctgtgacaaccagaggga ctgccagccg gggctgtgct gtgccttcca gagaggcctg ctgttccctgtgtgcacacc cctgcccgtg gagggcgagc tttgccatga ccccgccagc cggcttctggacctcatcac ctgggagcta gagcctgatg gagccttgga ccgatgccct tgtgccagtggcctcctctg ccagccccac agccacagcc tggtgtatgt gtgcaagccg accttcgtggggagccgtga ccaagatggg gagatcctgc tgcccagaga ggtccccgat gagtatgaagttggcagctt catggaggag gtgcgccagg agctggagga cctggagagg agcctgactgaagagatggc gctgggggag cctgcggctg ccgccgctgc actgctggga ggggaagagatttag The full-length sequence of Dkk-3 nucleotide or a fragment thereof can generally be obtained by methods like PCR amplification, recombination or artificial synthesis. For PCR amplification, the relevant sequence can be obtained by amplification with a primer (which is designed based on known nucleotide sequences of human Dkk-3, mouse Dkk-3 or rat Dkk-3, in particular open reading frame sequences) using the commercially available cDNA library or a cDNA sequence prepared by conventional methods known to those skilled in the art as a template. When the sequence is long, it is often necessary to perform PCR amplification twice or more, and then the amplified fragments are spliced together in the correct order.

Once the relevant sequence is obtained, the relevant sequence can be obtained in bulk using the recombination method. Usually this involves cloning the above-obtained relevant sequence into a vector, then transferring same into a cell, and then isolating the resulting relevant sequences from the proliferated host cells by conventional methods.

In addition, the relevant sequences can also be synthesized by artificial synthesis, especially when the fragment is short in length. In general, fragments with long sequences can be obtained by firstly synthesizing multiple small fragments and then ligating them.

At present, it has been possible to obtain the DNA sequence encoding the protein of the present invention (or a fragment thereof, or a derivative thereof) by chemical synthesis. The DNA sequence can then be introduced into a variety of existing DNA molecules (e.g., vectors) and cells known in the art. In addition, mutations can also be introduced into the protein sequences of the present invention by chemical synthesis.

The Dkk-3 protein can be obtained by introducing an encoding sequence corresponding to the Dkk-3 protein useful in the present invention into a host cell (directly introduced or by introducing a vector containing the Dkk-3 encoding sequence) and culturing the transformed host cells under appropriate conditions to express the Dkk-3 protein, and then isolate and purify the Dkk-3 protein.

Antibody Against the Dkk-3 Protein

In another aspect, the present invention also encompasses polyclonal and monoclonal antibodies, in particular monoclonal antibodies, that are specific to polypeptides encoded by Dkk-3 DNA or fragments thereof. Herein, "specificity" means the ability of the antibody binds to the product or fragment of the Dkk-3 gene. Preferably, the antibody refers to those bind to the product or fragment of the Dkk-3 gene but do not recognize or bind to other non-relevant antigen molecules. Antibodies in the present invention include molecules capable of binding and inhibiting the DKK-3 protein, as well as antibodies that do not affect the function of the Dkk-3 protein.

The present invention includes not only intact monoclonal antibodies, but also antibody fragments with immunogenic activity, such as Fab1 or Fab2 fragments; antibody heavy chains; antibody light chains; or chimeric antibodies, such as an antibody having the murine antibody binding specificity but still retaining the antibody moiety from humans.

The antibodies of the present invention can be prepared by various techniques known to those skilled in the art.

Antibodies against the Dkk-3 protein can be used in immunohistochemistry to detect Dkk-3 protein in biopsy specimens. In addition, monoclonal antibodies that bind to human Dkk-3 protein can also be labelled with radioisotopes or fluorescence, and then injected into the body to track their position and distribution. This radioactive or fluorescently labelled antibody can be used as a noninvasive diagnostic method for locating amyotrophic cells.

The antibodies of the present invention can be used to detect diseases associated with human Dkk-3 proteins, such as age-related muscle atrophy. Antibodies can also be used to design inhibitors for a particular site in the body. Monoclonal antibodies with high affinity for human Dkk-3 proteins can be covalently bound to the inhibitors. Since the Dkk-3 protein of the present invention is specifically highly-expressed in myocytes or muscle tissues, such hybrid antibodies can be used to reduce the level of human Dkk-3 protein.

Production of polyclonal antibodies can be applied in animals immunized with human Dkk-3 protein or polypeptide, such as rabbits, mice, rats and the like. A variety of adjuvants may be used to enhance the immune response, including but not limited to the Freund's adjuvant.

Pharmaceutical Composition

An antagonist (e.g., an antibody) of the protein of the present invention may provide a therapeutic effect when administered (dosed) on a therapeutic basis. Typically, these substances are configured in a non-toxic, inert and pharmaceutically acceptable aqueous carrier medium where the pH is generally from about 5 to about 8, preferably from about 6 to about 8, although the pH may vary depending on the nature of the substances being configured and the condition to be treated. The configured pharmaceutical compositions may be administered by conventional routes including, but not limited to, intramuscular, intraperitoneal, intravenous, subcutaneous, intradermal, or topical administration.

Antagonists of the polypeptides of the invention are useful in the treatment of age-related muscle atrophy. When the Dkk-3 protein of the present invention is used, other therapeutic agents may be used at the same time.

The present invention further provides a pharmaceutical composition comprising a safe and effective amount (e.g., 0.01 wt %-99 wt %) of the antagonist of the Dkk-3 protein of the present invention and a pharmaceutically acceptable carrier or excipient. Pharmaceutically acceptable excipients include, but are not limited to, pharmaceutically acceptable carriers, diluents, fillers, binders and other excipients. Therapeutically inert inorganic or organic carriers known to those skilled in the art include, but are not limited to, lactose, corn starch or derivatives thereof, talc, vegetable oil, wax, fat, polyhydroxy compounds (such as polyethylene glycol, water, sucrose, ethanol, glycerol, and the like), various preservatives, lubricants, dispersants, and flavoring agents. Humectants, antioxidants, sweeteners, colorants, stabilizers, salts, buffers, and the like may also be added thereto. These substances are used to enhance the stability of the formula as needed or to help improve the activity or its bioavailability or to produce an acceptable taste or flavour in the case of oral administration.

The pharmaceutical compositions of the present invention may be oral preparations such as capsules, tablets, dispersible tablets, buccal tablets, chewable tablets, effervescent tablets, sustained release tablets, granules and the like. Thus, shortcomings in the traditional decoction such as unpleasant appearance, inconvenience to carry, trouble in taking the medicine, and large intake amount are effectively improved, and a new approach is provided for the development of new formulations for chronic nephritis of small doses, strong efficacy, and good stability.

The pharmaceutical compositions of the present invention can be prepared by conventional methods, such as mixing the effective ingredients, or by conventional preparation methods for various preparations, such as mixing effective ingredients with the corresponding auxiliary materials. The pharmaceutical compositions of the present invention may also be used with other therapeutic agents.

The pharmaceutical composition of the present invention can be used for treating age-related muscle atrophy.

The therapeutically effective dose of the pharmaceutical composition of the present invention should be determined further by taking such factors into account as route of administration, patient health status, and so on, which fall within the skill range of skilled physicians.

The polynucleotides of the human Dkk-3 protein can also be used for a variety of therapeutic purposes. Gene therapy techniques can be used to treat abnormalities in cell proliferation, development or metabolism (such as age-related muscle atrophy) caused by or represented by the abnormal expression of the Dkk-3 protein.

Oligonucleotides that inhibit human Dkk-3 mRNA (including antisense RNA and DNA) and nucleases are also within the scope of the present invention. A nuclease is an enzyme capable of specifically decomposing a particular RNA, and its mechanism is that the nuclease molecule is specifically hybridized with the complementary target RNA for endonuclease action. Antisense RNA and DNA and nuclease can be obtained by using any RNA or DNA synthesis technique that is available now.

Methods for introducing polynucleotides into muscle tissues or cells include: directly injecting the polynucleotides into in vivo muscle tissues, or introducing polynucleotides in vitro through a vector (e.g., a virus, a bacteriophage or a plasmid) into a cell, then transplanting same into the body, or introducing polynucleotides into gene knockout or competitive mutants produced after modifying the genome sequence by TALEN, CRSP/Cas9 or other gene editing methods, etc.

Using the protein of the present invention, a variety of conventional screening methods can be used to screen out the substance interacting with the Dkk-3 protein, such as inhibitors, agonists or antagonists and the like. In screening, the Dkk-3 protein can be added to a bioanalytical assay to determine whether or not the compound affects the interaction between the Dkk-3 protein and its receptor so as to further determine whether the compound is an antagonist or not. In addition, the test compound can be administered to the experimental animals along with the Dkk-3 protein, and the presence of animal muscle shrinking relative to the control indicates that the compound is an agonist or antagonist of the Dkk-3 protein.

The cell line highly expressing the Dkk-3 protein can also be prepared by loading the cDNA of the Dkk-3 gene into an expression vector and transfecting a mammalian cell line with the expression vector; and the Dkk-3 protein in this cell line is used as a target to screen for drugs that activate or inhibit the Dkk-3 protein. In addition, the test compound is added to the culture medium of the cell line expressing the Dkk-3 protein to detect the change in the expression level of Dkk-3 protein. Compounds that inhibit the expression of Dkk-3 protein can be used to treat age-related muscle atrophy.

Detection Methods

The present invention also relates to a diagnostic test method for quantitative and orientation detection of the level of human Dkk-3 protein. These tests are well known in the art and include immunofluorescence assays, immunohistochemistry assays, and radioimmunoassays. The level of Dkk-3 protein detected in the tests can be used as one of the indexes suggesting whether or not the subject has greater susceptibility to age-related muscle atrophy than the normal population.

A method for detecting the presence or absence of the Dkk-3 protein in a sample is performed based on the specificity of the Dkk-3 protein, comprising: contacting the sample with a Dkk-3 protein-specific antibody; observing the presence or absence of the antibody complex, and the presence of antibody complexes indicating that the Dkk-3 protein is present in the sample.

The polynucleotides encoding the Dkk-3 protein can be used for the diagnosis and treatment of Dkk-3 protein-related diseases. In terms of diagnosis, the polynucleotides encoding the Dkk-3 protein can be used to detect whether or not the Dkk-3 transcript are expressed or the abnormal expression of Dkk-3 transcript at the disease state. For example, the Dkk-3 DNA sequence can be used to hybridize to biopsy specimens to determine the abnormal expression of the Dkk-3 protein.

Hybridization techniques include Southern blotting, Northern blotting, in situ hybridization, and the like. These technical methods are all disclosed mature techniques, and the relevant kits can be obtained commercially. A portion or all of the polynucleotides of the present invention can be immobilized on a microarray or gene chip as a probe for differential expression analysis and gene diagnosis of genes in muscle tissues. The transcription product of Dkk-3 gene can also be detected by RT-PCR amplification in vitro with the Dkk-3 protein-specific primer.

Due to the high expression rate of Dkk-3 protein in age-related muscle atrophy, Dkk-3 polynucleotides, Dkk-3 protein and antibodies thereof, as well as Dkk-3 protein-related antagonists and agonists, and the like can provide a new therapeutic approach for age-related muscle atrophy, and thus it has huge prospect of application.

Kits

The present invention also provides a diagnostic kit for determining whether or not the Dkk-3 expression is abnormal. In a preferred example, a kit comprises a primer that specifically amplifies a Dkk-3 transcript and/or a specific antibody against Dkk-3. The kit may also contain instructions describing how to use the kit to detect the Dkk-3. The kit may further comprise any one or more of the following components: various markers or labeling reagents which assist in detection; reagents (including buffer) for PCR; reagents for immunological hybridization; and positive and negative controls, etc.

It will be understood that after the present invention reveals for the first time the correlation between the abnormal expression of Dkk-3 gene and age-related muscle atrophy, a person skilled in the art can conveniently design a primer capable of specifically amplifying Dkk-3, and then determine the expression level by quantitative detection or the like. In general, the primer is 15 to 50 bp in length, preferably 18 to 30 bp. Although it is preferred that primers are completely complementary to the template, those skilled in the art know that, in the case where the primers are not complementary to the template (especially the 5' terminus of the primer) to some extent, the specific amplification is also possible (i.e., only the desired fragment is amplified). Kits containing these primers and methods using these primers are within the scope of the present invention.

Although the length of the amplification product is not particularly limited, the amplification product is usually 100 to 3,000 bp in length, preferably 150 to 2,000 bp, more preferably 200 to 1,000 bp.

Compared with other methods currently available for amyotrophic diagnosis, the advantages of the present invention are mainly manifested in: the correlation between Dkk-3 and age-related muscle atrophy, wherein the Dkk-3 is highly expressed in more than 90% of amyotrophic cases with a ratio of Dkk-3 expression in amyotrophic cells to Dkk-3 expression in normal cells>3.0:1, and the present method is significantly superior to the existing diagnostic methods in sensitivity and accuracy regarding detection, which is the first molecular diagnostic method available for detecting age-related muscle atrophy, and is also easy in operation.

Other advantages and effects of the present invention will be readily apparent to those skilled in the art from the following disclosure of the present invention by way of specific embodiments thereof. The present invention may also be practiced or applied by further different embodiments, and the details in this specification may be modified or varied without departing from the spirit of the invention on the basis of different views and applications.

Before further describing the specific embodiments of the present invention, it is to be understood that the scope of the invention is not limited to the specific embodiments described below; it should also be understood that terms used in the embodiments of the present invention are intended to describe particular specific embodiments and not to limit the scope of the invention; in the specification and claims of the present invention, the singular forms "one", "a/an", and "this" include plural forms unless expressly indicated otherwise.

When a numerical range is given in an embodiment, it is to be understood that the two endpoints of each numerical range and any value between the two endpoints can be selected, unless otherwise stated in the present invention. Unless defined otherwise, technical and scientific terms used herein have the same meaning as is commonly understood by one of skill in the art. In addition to the specific methods, apparatus and materials used in the embodiments, according to the mastery of the prior art and the description of the present invention by those skilled in the art, the present invention may also be practiced using any of the methods, apparatus and materials of the prior art that are similar to or equivalent to the methods, apparatus, materials described in the embodiments of the present invention.

Unless otherwise stated, an experimental method, a detection method, and a preparation method as disclosed in the present invention all employ conventional molecular biology, biochemistry, chromatin structure and analysis, analytical chemistry, cell culture, and recombinant DNA techniques in present technical field as well as conventional techniques in related fields. These techniques have been well documented in the existing literature, and for details, reference is made to Sambrook et al., MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, Chromatin (P. M. Wassarman and A. P. Wolffe, eds.), Academic Press, San Diego, 1999; and METHODS IN MOLECULAR BIOLOGY, Vol. 119, Chromatin Protocols (P. B. Becker, ed.) Humana Press, Totowa, 1999, etc.

Embodiment 1 High Expression of DKK-3 in Age-Related Muscle Atrophy (1) Detection of the presence or absence of high expression level of the Dkk-3 in senile muscles by RT-qPCR. The senile muscles were taken out, total RNA was extracted, and cDNA was obtained after subjecting same to reverse transcription. The level of Dkk-3 mRNA was detected by real-time quantitative PCR (qPCR) using cDNA as a template, and then compared with the level of Dkk-3 in young muscle. If the expression level increased more than 3 times, it is determined that the expression level of Dkk-3 increased.

Specific experimental methods: 40 samples of muscle samples from the elderly (>65 years) and 10 (<50 mg) from adults (18-30 years) were taken and placed in 1.5 ml of Eppendorf Tube® (EP) tube, 1 ml of TRIzol® was added, and the mixture was shaken well by a tissue homogenizer for 2 minutes. The mixture was centrifuged at 4° C. for 10 minutes at 13,200 rpm/min and the supernatant was transferred to another clean Eppendorf Tube® (EP) tube. 200 µl of phenol:chloroform (24:1) was added, the tube contents were mixed thoroughly by vortexing, and centrifuged at 13,200 rpm/min at 4° C. for 15 minutes. The supernatant was transferred to a clean Eppendorf Tube® (EP) tube, 500 µl of isopropanol was added, and the mixture was thoroughly mixed and centrifuged at 13,200 rpm/min at 4° C. for 15 minutes. The supernatant was discarded and the precipitate was washed twice with 75% ethanol, each with centrifugation at 13,200 rpm/min at 4° C. for 5 minutes. The supernatant was discarded and the precipitate was kept at room temperature for 5-10 minutes to dryness, and 30-50 µl of aqueous DEPC was added to dissolve the dry contents to obtain the total RNA. The total RNA was then subjected to reverse transcription into cDNA. 1 µg of RNA was taken, 1 µl (200 units) of MuLV reverse transcriptase and 1× reaction buffer (New England Biolabs® (NEB®) company), 0.5 mM of dNTP mixture, 4 µM of Oligo dT, and 1µl of RNase inhibitor were added and incubated at 42° C. for 1 hour, and was then subjected to reverse transcription into cDNA. The cDNA was inactivated at 90° C. for 10 minutes and then used as a PCR template. Real-time quantitative PCR was used to detect the expression level of the target gene using the forward and reverse primers as shown in SEQ ID NOs: 3 and 4. The PCR was carried out as follows: 95° C. for 10 minutes, 95° C. for 30 seconds, 60° C. for 60 seconds, wherein the second and third steps were repeated for 40 times.

```
Forward primer:
                                      SEQ ID NO. 3
tgaggcagtggctacacaag Reverse primer:
                                      SEQ ID NO. 4
gctggtatggggttgagaga
```

Using GAPDH as the internal reference, the primer sequence used is as follows

```
GAPDH forward:
                                      SEQ ID NO. 5
ACCCAGAAGACTGTGGATGG GAPDH reverse:
                                      SEQ ID NO. 6
ACACATTGGGGGTAGGAACA
```

At the same time, the expression of muscle atrophy-specific gene atrogin was detected intramuscularly and acts as a marker of muscle atrophy. The primers used are:

```
Atrogin-1 forward:
                                      SEQ ID NO. 7
AGAGAGGCAGATTCGCAAGCGT Atrogin-1 reverse:
                                      SEQ ID NO. 8
TGCAAAGCTGCAGGGTGACCC
```

Figure 1:
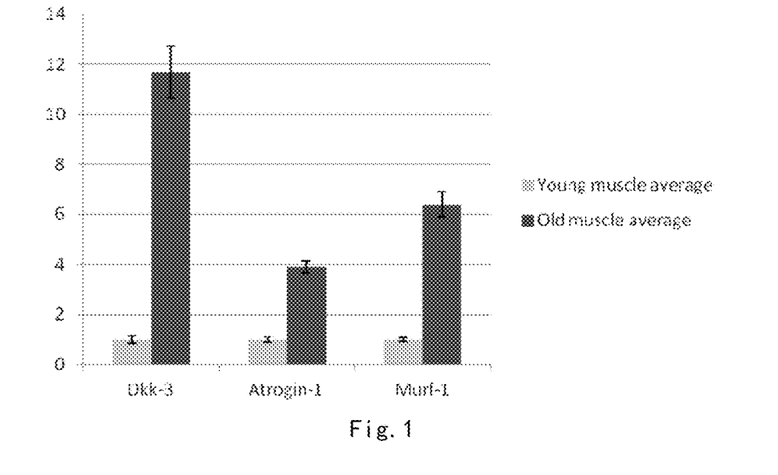
FIG. 1: A remarkable increase in the expression level of muscular Dkk-3 was seen in the elderly, and a surge in the expression levels of muscle atrophy-specific genes Atrogin-1 and MuRF-1 was also seen in the elderly.

According to RT-qPCR results as shown in FIG. 1, a remarkable increase in the expression level of muscular Dkk-3 was seen in the elderly (i.e., the expression level of Dkk-3 in amyotrophic muscles was 11.83 times of that in normal muscles), and a surge in the expression level of muscle atrophy-specific gene atrogin-1 was also seen in the elderly.

(2) Determination of the relationship between the expression level of Dkk-3 and the muscular diameter by immunofluorescent staining. Senile (65-year-old) muscles were taken, and OCT embedded for later use as frozen sections. Immunofluorescent staining was performed on the Dkk-3 antibody and laminin B antibody. The Dkk-3 antibody staining showed the expression level of Dkk-3, and the laminin B staining showed the profile of muscle fibers. The relationship between the expression level of Dkk-3 and the area of muscle fibers was determined by the calculated area of muscle fibers.

Figure 2:
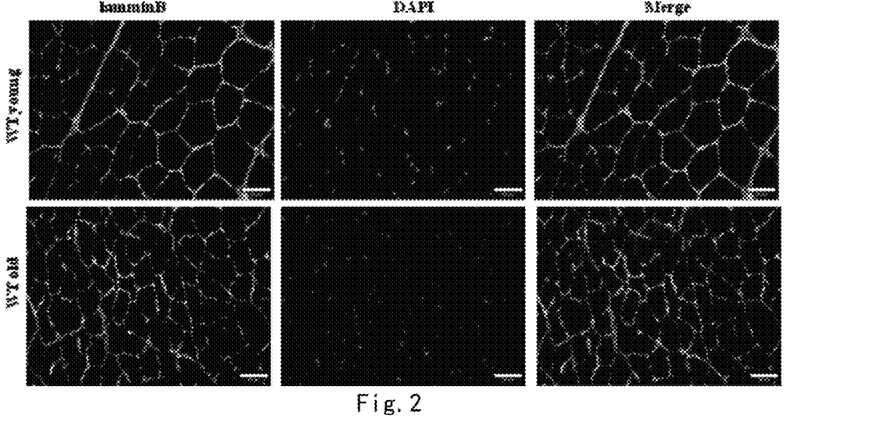
FIG. 2: The laminin B immunofluorescent staining showed that the area of senile muscle fibers was significantly smaller than that of young muscle fibers. Scale bar: 20 μm.
Figure 3:
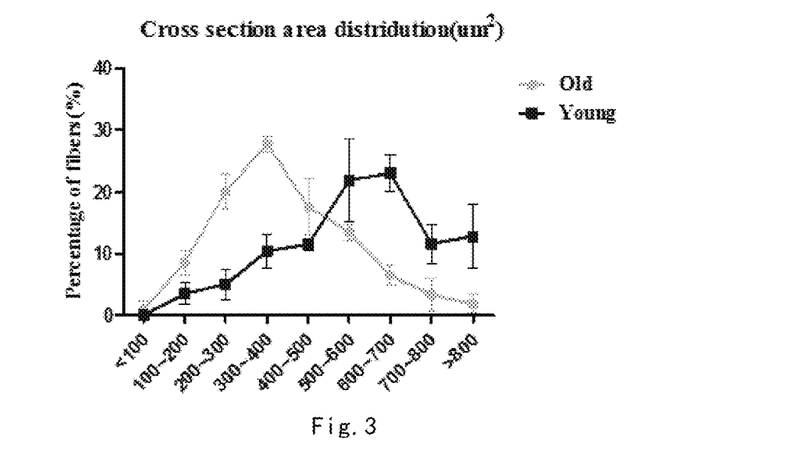
FIG. 3: The statistical analysis showed that the area of senile muscle fibers was significantly smaller than that of young muscle fibers.

The senile or adult muscle weighing less than 100 mg was embedded in the OCT and placed in liquid nitrogen for 30 seconds to prepare a frozen sample which can be made into frozen sections of 8 µm. The sections were subjected to laminin B immunofluorescent staining to determine the profile of muscle fibers and calculate the size of muscle fibers. The staining method was as follows: frozen sections were washed three times with PBS. The sections were fixed with 4% formaldehyde, and kept at room temperature for 15 minutes. The sections were washed three times with PBS, 1% Tween® 20 (Polysorbate 20) was added and kept at room temperature for 10 minutes. The sections were washed three times with PBS, the Laminin antibody diluted 200-fold in PBS containing 1% BSA was added, and incubated at room temperature for 1 hour. The sections were washed three times with PBS, each for 5 minutes. The fluorescent labeled donkey anti-rabbit secondary antibody diluted 1:1000 in 1% BSA-containing PBS solution was added, and incubated at room temperature for 1 hour. The mixture was washed once with PBS, PBS containing 20 µM of DAPI was added and kept at room temperature for 5 minutes, and then washed three times with PBS, each for 5 minutes. An anti-quencher was added before sealing. The sealed sample was observed and photographed under a Zeiss® laser confocal microscope. As shown in FIG. 2, the senile muscle fibers were significantly smaller. According to the results of statistical analysis as shown in FIG. 3, the senile muscle fibers of mice were significantly smaller.

Embodiment 2 the Correlation Between Dkk-3 and Muscle Atrophy

It has been found that the expression level of Dkk-3 in adult (<60 years) muscles is low, while the expression level of Dkk-3 in senile (>65 years) muscles is significantly higher than that in adult muscles. In cellular experiments, it has been found that the expression level of Dkk-3 either in myotube of the original muscle fibers directly separated in vivo or in terminally differentiated myotube obtained by in vitro induced differentiation of muscle stem cells is low. The overexpression of Dkk-3 in the terminally differentiated myotube resulted in muscle atrophy. According to in vivo experiments, the overexpression of Dkk-3 through adenovirus vectors in mouse muscles can also give rise to muscle atrophy.

Cellular experiments:

(1) Configuration of growth medium: To DMEM high glucose medium was added 10% fetal bovine serum and mixed uniformly for standby use.

(2) Configuration of differentiation medium: To DMEM high glucose medium was added 2% horse serum and mixed uniformly for standby use.

(3) Packaging adenovirus capable of expressing DKK-3 (titer: $1.3 \times 10^{10}$ Tu/ml), the method being described below in more specific details:

The DKK-3 CDS sequence (NM 015814) was firstly obtained from NCBI and PCR primers were designed as below:

primer-F:
(SEQ ID NO. 9)
GGGGTACCATGGACTACAAAGACCATGAC;

primer-R:
(SEQ ID NO. 10)
GCTCTAGACTAAATCTCCTCCTCTCCGCC;

C2C12 cells in a 10 cm petri dish were taken, the culture medium was discarded, and 1 ml of TRIzol® was added for cell lysis; 200 µl of chloroform was added and shaken well, centrifuged at 12,000 rpm/min at 4° C. for 15 minutes, and the upper clear liquid was transferred into a new Eppendorf Tube® (EP) tube; 500 µl of isopropanol was added and mixed uniformly, centrifuged at 12,000 rpm/min at 4° C. for 15 minutes, the supernatant was discarded, and the precipitate was washed once by addition of 1 ml of 75% ethanol, and after the supernatant was discarded, the precipitate was aired at room temperature for 10 minutes; 40 µl of RNase-free water was added to dissolve the dry contents to obtain the total mRNA. After the mRNA concentration was determined by spectrophotometry, 1 µg of the total RNA was taken, 1 µl (200 units) of MuLV reverse transcriptase and 1× reaction buffer (NEB® company), 0.5 mM of dNTP mixture, 4 µM of Oligo dT, and 1 µl of RNase inhibitor were added and incubated at 42° C. for 1 hour, and was then subjected to reverse transcription into cDNA. The cDNA was inactivated at 75° C. for 10 minutes and then used as a PCR template. Genes expressing DKK-3 were obtained by PCR using the well-designed PCR primes with addition of 1 µl of KOD polymerase and 1 µl (10 mM) of dNTP (1. 95° C. for 5 min; 2. denaturation at 95° C. for 30 s; 3. annealing at 58° C. for 30 s; 4. extension at 68° C. for 2 min; 5. 68° C. for 10 min, wherein steps 2-4 were repeated for 30 times). The PCR product was recovered by agarose gel electrophoresis and digested with 1 µl of Kpn1 and Xbal1 restriction endonuclease (NEB® company) at 37° C. for 2 hours, 1 µg of the vector padTrack-GFP was also digested with 1 µl of Kpn1 and Xbal1 restriction endonucleases (NEB® company) at 37° C. for 2 hours, and after being recovered by agarose gel electrophoresis and ligated with 1 µl of T4 DNA ligase (NEB® company) at room temperature for 5 hours, the PCR product was used to transform the competent cell BJ5183 which was then used to transfect the DH5α competent cell for plasmid amplification after being identified by digestion with Kpn1 and Xbal1 restriction endonucleases, and the plasmids were extracted and linearized with Pac1 restriction endonuclease, which were then used after gel extraction to transfect the cell 293A which packages viruses. 10 µg of linearized expression plasmids were taken, and 293A cells were transfected by calcium phosphate precipitation method: 10 µg of plasmids were added into 250 µl of water, and 250 µl of calcium chloride solution was added, fully mixed for standby use; to a 50 ml of centrifuge tube was added 500 µl of 2× HBS solution, and the prepared plasmid-calcium solution was added dropwise to the HBS solution with shaking; the mixture was then kept at room temperature for 20 minutes for standby use; 293A cells with an attachment rate of about 60% of the basal area were taken and residual culture fluid thereon was absorbed, 10 ml of growth culture medium (DMEM+10% FBS) was added, the previously prepared plasmid-calcium precipitate suspension was slowly added, shaken gently and mixed uniformly, and then placed in a incubator with 5% carbon dioxide at 37° C.; 16 hours after transfection, the growth medium was changed for new and the cultivation continued. After 48 hours, the culture was observed daily under a fluorescence microscope until all cells under the microscope expressed green fluorescence (typically 7-10 days). All cells and cell culture fluid were collected, centrifuged at 1500 rpm/min at room temperature for 5 minutes, the supernatant was discarded and the cell precipitate was retained. The precipitate was washed twice with PBS, resuspended by addition of 500 µl of PBS, the cells were thawed by a freezing-thawing method with liquid nitrogen at −37° C. (freeze-thawing for 3 times), centrifuged at 2,000 rpm/min at room temperature for 5 minutes, and the supernatant was transferred into a new tube for standby use (i.e., viruses of passage 1 (P1)). 40 plates (10 cm petri dish) of 293A cells were cultured until reaching an attachment rate of about 60% of the basal area, to each plate was added 10 µl of viruses of passage 1 (P1), and after 24 hours, the culture was observed daily under a microscope until all cells expressed green fluorescence (typically 2-3 days), and viruses of passage 2 (P2) were collected, thawed and released in a similar manner for obtaining viruses of passage 1 (P1) (generally, 2 ml of PBS was added for cell lysis to obtain the virus). The obtained viruses can be used immediately after being titrated (if more viruses are needed later, amplification can be employed according to the method for obtaining viruses of passage 2 (P2)).

(4) Cell line culture: C2C12 cells were taken from the liquid nitrogen and quickly dissolved in a 37° C. water bath, then added into 9 ml of growth medium, centrifuged at 1500 rpm/min at room temperature for 5 minutes, the supernatant was discarded, 1 ml of growth medium was added for resuspension and then transferred into a 10 cm petri dish, another 9 ml of growth medium was added, and cultured under 5% carbon dioxide at 37° C. Differentiation of C2C12 cell lines into myotube: when the C2C12 cells covered the whole petri dish, the culture was washed three times with PBS, and 10 ml of differentiation medium was added for induced differentiation under 5% carbon dioxide at 37° C. for 3 days.

Figure 4A:
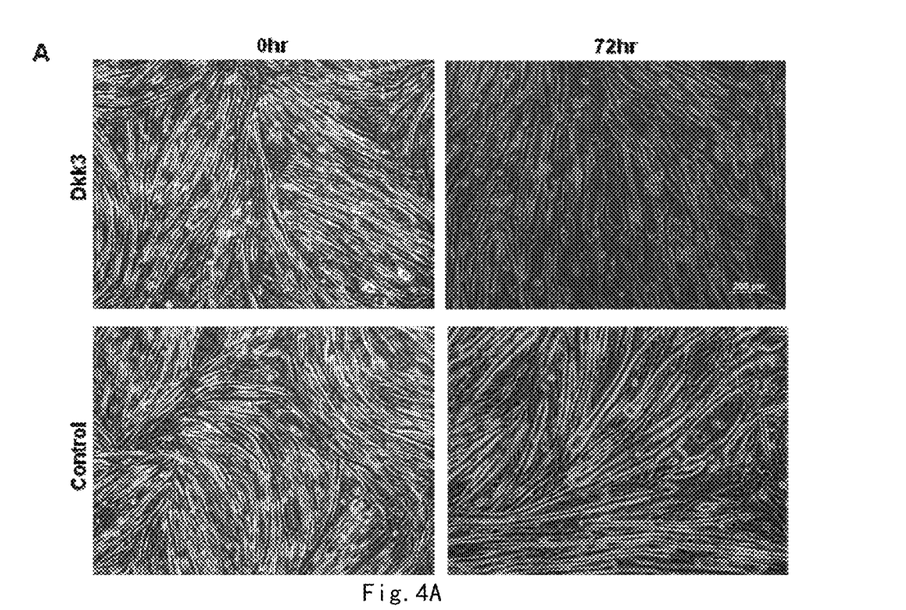
FIG. 4A: The diameter of the myotube was significantly reduced after the overexpression of Flag-labelled Dkk-3 compared to the control group.
Figure 4B:
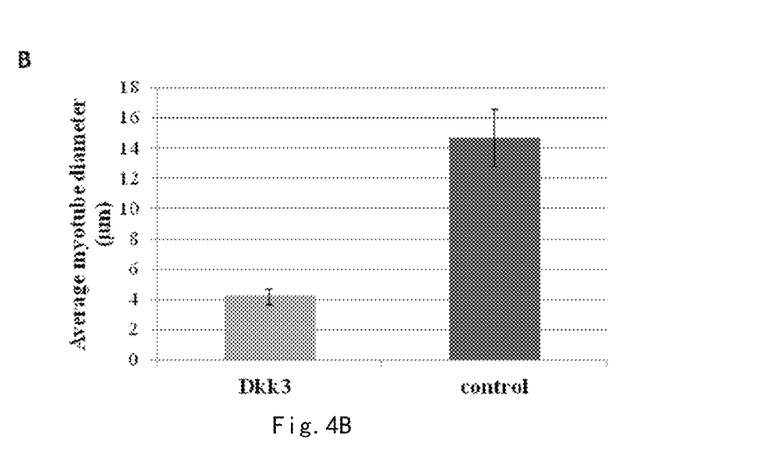
FIG. 4B: The statistical analysis showed that the diameter of the myotube was significantly reduced after the overexpression of Dkk-3.
Figure 4C:
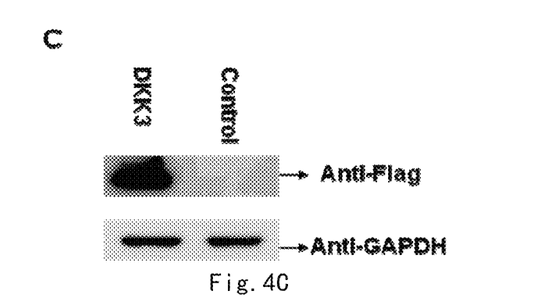
FIG. 4C: The overexpression level of Flag-labelled Dkk-3 in the myotube was detected by Western blot.

(5) Muscle atrophy in myotube differentiated from C2C12 induced by overexpression of Dkk-3: the 10 ml of differentiation medium was changed for new, 10 µl of PBS was added to the control group, Dkk-3 adenovirus (titer: 1.3× $10^{10}$ TU/ml, MOI:1:5) was added to the experimental group, and cultured under 5% carbon dioxide at 37° C. for 72 hours. The culture was observed and photographed under a Zeiss® fluorescence microscope, and the diameter of myotube was measured (FIGS. 4A and B). At the same time, cells were collected and total protein was extracted, 40 µg of total protein was taken for SDS-PAGE electrophoresis, hybridized with the Flag antibody after membrane transfer (1:2000 dilution, at room temperature for 1 hour), and the overexpressed Flag-labeled Dkk-3 was detected. The hybridization was washed three times with PBS (each for 10 minutes), the donkey anti-mouse secondary antibody (1:1000 dilution) was added, and incubated at room temperature for 1 hour. The hybridization was washed three times with PBS (each for 10 minutes), developed, and the expression of the overexpressed Flag-labeled Dkk-3 was detected (FIG. 4C).

According to the results as shown in FIG. 4A, the diameter of the myotube was significantly reduced after the overexpression of Flag-labelled Dkk-3 compared to the blank control group. FIG. 4B: The statistical analysis showed that the diameter of the myotube was significantly reduced after the overexpression of Dkk-3. FIG. 4C: The overexpression of Flag-labelled Dkk-3 in the myotube was confirmed by Western blot.

(6) A plate of cells was taken from the experimental group with the Dkk-3 adenovirus being added and the control group separately, total RNA was extracted after addition of 1 ml of TRIzol®, 1 µg of total RNA was taken from the two groups respectively, 1 µl (200 units) of MuLV reverse transcriptase and 1× reaction buffer (NEB® company), 0.5 mM of dNTP mixture, 4 µM of Oligo dT, and 1 µl of RNase inhibitor were added and incubated at 42° C. for 1 hour, and was then subjected to reverse transcription into cDNA. The cDNA was inactivated at 90° C. for 10 minutes and then used as a PCR template. Real-time quantitative PCR was used to detect the expression level of the target gene using the forward and reverse primers as listed above. The PCR was carried out as follows: 95° C. for 10 minutes, 95° C. for 30 seconds, 60° C. for 60 seconds, wherein the second and third steps were repeated for 40 times. Using GAPDH as the internal reference, the primer sequence used is as follows:

```
GAPDH forward:
                                   (SEQ ID NO. 5)
ACCCAGAAGACTGTGGATGG GAPDH reverse:
                                   (SEQ ID NO. 6)
ACACATTGGGGGTAGGAACA
```

At the same time, the expression of muscle atrophy-specific genes Atrogin1 (NM_026346.3) and Atrogin1 (NM_026346.3) was detected intramuscularly and acts as a marker of muscle atrophy.

The primer sequences used are:

```
Atrogin-1 forward:
                                   (SEQ ID NO. 7)
AGAGAGGCAGATTCGCAAGCGT Atrogin-1 reverse:
                                   (SEQ ID NO. 8)
TGCAAAGCTGCAGGGTGACCC
```

Figure 5:
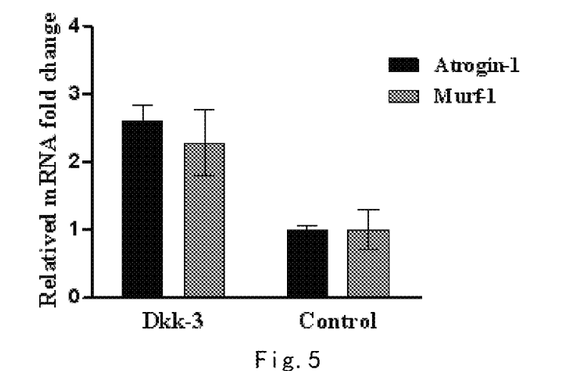
FIG. 5: The overexpression of Dkk-3 in the myotube cultured in vitro resulted in increased expression of muscle atrophy-specific genes Atrogin-1 and MuRF-1.

The Atrogin1 was subjected to reverse transcription into cDNA using the MuLv reverse transcriptase (NEB® company), and the mRNA expression level of Atrogin1, the muscle atrophy marker, was measured by real-time fluorescence quantitative PCR. According to the results as shown in FIG. 5, the overexpression of Dkk-3 can upregulate the expression level of Atrogin1, thus resulting in muscle atrophy.

Animal Experiments:

The GFP-labeled DKK-3 adenovirus (titer: 1.3×$10^{10}$ Tu/ml) was expressed.

The method for packaging the adenovirus capable of expressing DKK-3 (titer: 1.3×$10^{10}$ Tu/ml) is described below in more specific details:

the DKK-3 CDS sequence (NM 015814) was firstly obtained from NCBI and PCR primers were designed as below:

```
primer-F:
                                   (SEQ ID NO. 7)
GGGGTACCATGGACTACAAAGACCATGAC;

primer-R:
                                   (SEQ ID NO. 7)
GCTCTAGACTAAATCTCCTCCTCTCCGCC.
```

C2C12 cells in a 10 cm petri dish were taken, the culture solution was discarded, and 1 ml of TRIzol® was added for cell lysis; 200 µl of chloroform was added and shaken well, centrifuged at 12,000 rpm/min at 4° C. for 15 minutes, and the upper clear liquid was transferred into a new EP tube; 500 µl of isopropanol was added and mixed uniformly, centrifuged at 12,000 rpm/min at 4° C. for 15 minutes, the supernatant was discarded, and the precipitate was washed once by addition of 1 ml of 75% ethanol, and after the supernatant was discarded, the precipitate was aired at room temperature for 10 minutes; 40 µl of RNase-free water was added to dissolve the dry contents to obtain the total mRNA. After concentration measurement, 1 µg of the total RNA was taken, 1 µl (200 units) of MuLV reverse transcriptase and 1× reaction buffer (NEB® company), 0.5 mM of dNTP mixture, 4 µM of Oligo dT, and 1 µl of RNase inhibitor were added and incubated at 42° C. for 1 hour, and was then subjected to reverse transcription into cDNA. The cDNA was inactivated at 75° C. for 10 minutes and then used as a PCR template. The gene expressing DKK-3 was obtained by PCR using the well-designed PCR primes, the obtained gene was digested with Kpn1 and Xbal1 restriction endonucleases at 37° C. for 2 hours, the vector padTrack-GFP was also digested with the Kpn1 and Xbal1 restriction endonucleases at 37° C. for 2 hours, and after being recovered by agarose gel electrophoresis and ligated with T4 DNA ligase at room temperature for 5 hours, the gene was used to transform the competent cell BJ5183 which was then used to transfect the DH5a competent cell for plasmid amplification after being identified by digestion with Kpn1 and Xbal1 restriction endonucleases, and the plasmids were extracted and linearized with Pac 1 restriction endonuclease, which were then used after gel extraction to transfect the cell 293A which packages viruses. 10 µg of linearized expression plasmids were taken, and 293A cells were transfected by calcium phosphate precipitation method: 10 µs of plasmids were added into 250 µl of water, and 250 µl of calcium chloride solution was added, fully mixed for standby use; to a 50 ml of centrifuge tube was added 500 µl of 2×HBS solution, and the prepared plasmid-calcium solution was added dropwise to the HBS solution with shaking; the mixture was then kept at room temperature for 20 minutes for standby use; 293A cells with an attachment rate of about 60% of the basal area were taken and residual culture fluid thereon was absorbed, 10 ml of growth culture medium (DMEM+10% FBS) was added, the previously prepared plasmid-calcium precipitate suspension was slowly added, shaken gently and mixed uniformly, and then placed in a incubator with 5% carbon dioxide at 37° C.; 16 hours after transfection, the growth medium was changed for new and the cultivation continued. After 48 hours, the culture was observed daily under a fluorescence microscope until all cells under the microscope expressed green fluorescence (typically 7-10 days). All cells and cell culture fluid were collected, centrifuged at 1,500 rpm/min at room temperature for 5 minutes, the supernatant was discarded and the cell precipitate was retained. The precipitate was washed twice with PBS, resuspended by addition of 500 µl of PBS, the cells were thawed by freezing-thawing method with liquid nitrogen at −37° C. (freeze-thawing for 3 times), centrifuged at 2,000 rpm/min at room temperature for 5 minutes, and the supernatant was transferred into a new tube for standby use (i.e., viruses of passage 1 (P1)). 40 plates (10 cm petri dish) of 293A cells were cultured until reaching an attachment rate of about 60% of the basal area, to each plate was added 10 µl of viruses of passage 1 (P1), and after 24 hours, the culture was observed daily under a microscope until all cells expressed green fluorescence (typically 2-3 days), and viruses of passage 2 (P2) were collected, thawed and released in a similar manner of obtaining viruses of passage 1 (P1) (generally, 2 ml of PBS was added for cell lysis to obtain the virus). The obtained viruses can be used immediately after being titrated (if more viruses are needed later, amplification can be employed according to the method for obtaining viruses of passage 2 (P2)).

Figure 6A:
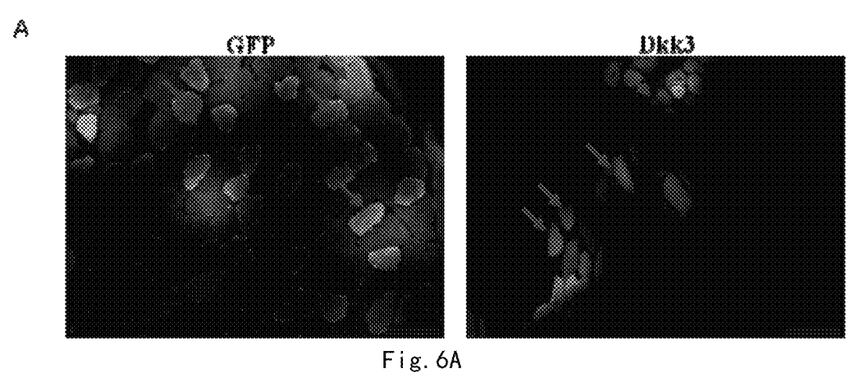
FIG. 6A: The overexpression of GFP-labelled Dkk-3 in mouse muscles resulted in a significant reduction in muscle fiber area at the injection site.
Figure 6B:
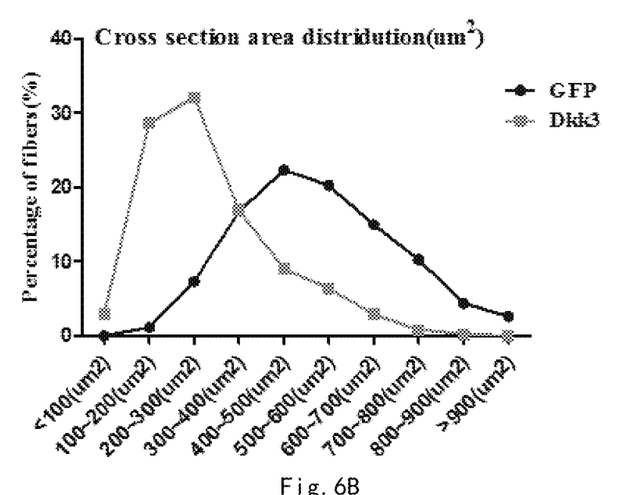
FIG. 6B: Statistical analysis of muscle fiber area after the overexpression of Dkk-3. The overexpression of GFP-labelled Dkk-3 resulted in a significant reduction in muscle fiber area at the injection site.

Method: 50 µl of the adenovirus expressing DKK-3 (titer: $1.3\times10^{10}$ TU/ml) was injected intramuscularly into the tibialis anterior of the mouse left leg, and similarly 50 µl of empty vector adenovirus (titer: $1.3\times10^{10}$ TU/ml) was injected into the tibialis anterior of the right leg once a day, continuously for 7 days. 10 days after the completion of injection, the tibialis anterior of the mouse was then taken and embedded in the embedding medium OCT for preparation of frozen sections. The profile of the muscle fibers were displayed by hematoxylin-eosin staining (HE staining) for comparing the diameter of muscle fibers. Staining method is as follows: The frozen section was washed twice with PBS, each for 5 minutes; stained with hematoxylin for 1 minute, and rinsed with tap water for 20 minutes; incubated in 30% ethanol for 5 minutes; incubated in 50% ethanol for 5 minutes; incubated in 70% ethanol for 5 minutes; incubated in 95% ethanol for 5 minutes; dyed in eosin dyes for 10 seconds; incubated in 95% ethanol for 5 minutes; incubated in 100% ethanol for 5 minutes; incubated in 100% ethanol for 5 minutes; incubated in the solution of xylene:EtOH=1:1 for 10 minutes; incubated in xylene for 10 minutes; and sealed with resin adhesive after drying. The muscle section was photographed under a microscope, and the diameter of muscle fibers was calculated and recorded (FIG. 6). Specifically, as shown in FIG. 6A, the overexpression of GFP-labelled Dkk-3 in mouse muscles triggered muscle atrophy. According to the statistical analysis as shown in FIG. 6B, the muscular diameter in groups with overexpression of GFP-labelled Dkk-3 was remarkably smaller than that in groups with mere expression of GFP.

Embodiment 3 Preparation of Kits

As described in Embodiments 1 and 2, the abnormal expression of the Dkk-3 protein is closely related to muscle atrophy. Accordingly, amplification can be performed with Dkk-3 gene-specific primers using the patient's DNA as a template for detection.

The kit (for 100 users) was prepared, said kit comprising:

| Name | Sequence | Concentration |
| --- | --- | --- |
| Forward primer | SEQ ID NO. 3 | 100 µM |
| Reverse primer | SEQ ID NO. 4 | 100 µM |

Muscular tissues were extracted from the patient to be tested, mRNA was then extracted by conventional methods or by using specific extraction kits, and subjected to reverse transcription into cDNA. The PCR primers of the muscle atrophy kit were diluted and detected for the expression level of DKK-3, which was compared with that of the normal control, so as to further determine the expression level of the DKK-3 protein.

According to the detection results, the subject whose expression level of the Dkk-3 protein is higher than that of the normal control (3 times higher) has higher susceptibility to muscle atrophy than the normal population.

Embodiment 4 Preparation of Kits

Preparation of Detection Kits

In the present embodiment, the detection kit was prepared with an antibody against the Dkk-3 protein:

As described in Embodiments 1 and 2, the abnormal expression of the Dkk-3 protein is closely related to muscle atrophy. Accordingly, the expression of the DKK-3 protein in muscle tissues was detected by immunohistochemistry with the commercialized or self-prepared Dkk-3 antibody.

The kit (for 100 users) was prepared, said kit comprising:

| Contents | Quantity |
| --- | --- |

Goat anti-human Dkk-3 polyclonal antibody (purchased from R&D Systems®) 0.5 ml, concentration of 200 μg/ml 1:1000 dilution before use.

Frozen sections were firstly prepared with clinical fresh muscle specimens by conventional methods, the goat anti-human Dkk-3 polyclonal antibody was then added, incubated at room temperature, and detected for positive signals, to calculate and score the microscopic positive cell ratio, wherein the score that is 3 times greater than that of the normal muscle tissue is considered significantly different.

It turns out that Dkk-3 was highly expressed in more than 85% of cases with muscular atrophy (25 out of 28 cases of muscular atrophy), with the ratio of Dkk-3 expression level in amyotrophic tissues to that of normal muscle tissues ≥3.0.

The foregoing embodiments are intended to illustrate embodiments of the present disclosure and are not to be construed as limiting the invention. In addition, the various modifications listed herein, as well as variations in the methods and compositions of the present invention, will be apparent to those skilled in the art without departing from the scope and spirit of the invention. While the present invention has been particularly described in connection with a variety of specific preferred embodiments of the present invention, it is to be understood that the invention should not be limited to these specific embodiments. In fact, various inventions obtained through the above-described modifications that will be apparent to those skilled in the art are intended to be included within the scope of the invention.

The invention claimed is:

1. A method for detecting age-related muscle atrophy, wherein said method comprises: (1) detecting an amount of an encoding gene of a Dkk3 protein or a transcript thereof in myocytes or muscle tissues of a patient, wherein detecting the amount of the encoding gene of the Dkk-3 protein, or a transcript thereof comprises the use of SEQ ID NO: 3 and SEQ ID NO: 4 as amplification primers; and (2) comparing the amount of the encoding gene of the Dkk3 protein or the transcript thereof in the myocytes or muscle tissues of the patient in step (1) with the amount of the encoding gene of the Dkk3 protein or the transcript thereof in normal myocytes or muscle tissues, wherein a higher amount of the encoding gene of the Dkk3 protein or the transcript thereof in the myocytes or muscle tissues of the patient than the amount of the encoding gene of the Dkk3 protein or the transcript thereof in normal myocytes or muscle tissues indicates that the patient is suffering from age-related muscle atrophy or is susceptible to age-related muscle atrophy.

2. The method of claim 1, wherein detecting the amount of the Dkk-3 encoding gene or transcript comprises using quantitative PCR.

3. The method of claim 1, wherein the amino acid sequence of the Dkk-3 protein is SEQ ID NO: 1.

4. The method of claim 1, wherein the Dkk-3 protein is encoded by SEQ ID NO: 2.

5. An in vitro method for determining whether an expression level of a Dkk-3 gene in a test sample of myocytes or muscle tissues indicates age-related muscle atrophy, wherein the method comprises:

(1) extracting mRNA from the test sample of myocytes or muscle tissues and subjecting the mRNA to reverse transcription into a cDNA;

(2) obtaining an amplification product of the Dkk-3 gene through amplification by quantitative PCR using primers that specifically amplify the cDNA obtained in step (1), wherein the primers are SEQ ID NO: 3 and SEQ ID NO: 4; and (3) comparing the amount of the Dkk-3 amplification product obtained in step (2) with the amount of a Dkk-3 amplification product in a normal sample of myocytes or muscle tissues, wherein a higher amount of the Dkk-3 amplification product obtained in step (2) than the amount of the Dkk-3 amplification product in the normal sample of myocytes or muscle tissues indicates that the expression level of the Dkk-3 gene in the test sample of myocytes or muscle tissues is indicative of age-related muscle atrophy.

6. The in vitro method of claim 5, wherein the amino acid sequence encoding the Dkk-3 gene is SEQ ID NO: 1.

7. The in vitro method of claim 5, wherein the nucleic acid sequence of the Dkk-3 cDNA is SEQ ID NO: 2.

8. A method for detecting age-related muscle atrophy or susceptibility to age-related muscle atrophy, wherein said method comprises the following steps of:

obtaining an amplification product of Dkk-3 through amplification by quantitative PCR using primers that specifically amplify a Dkk-3 transcript or cDNA prepared from myocytes or muscle tissues of an individual to be tested, and examining whether the amount of amplification products is higher than that in a normal control, wherein the primers are SEQ ID NO: 3 and SEQ ID NO: 4;

wherein a higher amount of the formed amplification products of the individual than that in a normal control indicates that the individual is suffering from age-related muscle atrophy or has greater susceptibility to age-related muscle atrophy than the normal population.

9. The method of claim 8, wherein the amino acid sequence encoding the Dkk-3 transcript or cDNA is SEQ ID NO: 1.

10. The method of claim 8, wherein the nucleic acid sequence of the transcript or cDNA is SEQ ID NO: 2.

* * * * *

```
                        SEQUENCE LISTING

<160> NUMBER OF SEQ ID NOS: 10

<210> SEQ ID NO 1
<211> LENGTH: 350
<212> TYPE: PRT
<213> ORGANISM: Artificial Sequence
<220> FEATURE:
<223> OTHER INFORMATION: Human Dkk-3 protein

<400> SEQUENCE: 1

Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
            20                  25                  30

Lys Pro Gly Pro Ala Leu Ser Tyr Pro Gln Glu Glu Ala Thr Leu Asn
        35                  40                  45

Glu Met Phe Arg Glu Val Glu Glu Leu Met Glu Asp Thr Gln His Lys
    50                  55                  60

Leu Arg Ser Ala Val Glu Glu Met Glu Ala Glu Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
            100                 105                 110

Arg Glu Ile His Lys Ile Thr Asn Asn Gln Thr Gly Gln Met Val Phe
        115                 120                 125

Ser Glu Thr Val Ile Thr Ser Val Gly Asp Glu Glu Gly Arg Arg Ser
    130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
            180                 185                 190

Gly His Cys Thr Lys Met Ala Thr Arg Gly Ser Asn Gly Thr Ile Cys
        195                 200                 205
```

```
Asp Asn Gln Arg Asp Cys Gln Pro Gly Leu Cys Cys Ala Phe Gln Arg
    210                 215                 220
Gly Leu Leu Phe Pro Val Cys Thr Pro Leu Pro Val Glu Gly Glu Leu
225                 230                 235                 240
Cys His Asp Pro Ala Ser Arg Leu Leu Asp Leu Ile Thr Trp Glu Leu
                245                 250                 255
Glu Pro Asp Gly Ala Leu Asp Arg Cys Pro Cys Ala Ser Gly Leu Leu
                260                 265                 270
Cys Gln Pro His Ser His Ser Leu Val Tyr Val Cys Lys Pro Thr Phe
            275                 280                 285
Val Gly Ser Arg Asp Gln Asp Gly Glu Ile Leu Leu Pro Arg Glu Val
    290                 295                 300
Pro Asp Glu Tyr Glu Val Gly Ser Phe Met Glu Val Arg Gln Glu
305                 310                 315                 320
Leu Glu Asp Leu Glu Arg Ser Leu Thr Glu Glu Met Ala Leu Gly Glu
                325                 330                 335
Pro Ala Ala Ala Ala Ala Leu Leu Gly Gly Glu Glu Ile
            340                 345                 350
```

<210> SEQ ID NO 2
<211> LENGTH: 1053
<212> TYPE: DNA
<213> ORGANISM: Artificial Sequence
<220> FEATURE:
<223> OTHER INFORMATION: Sequence coding for Dkk-3 protein

<400> SEQUENCE: 2

```
atgcagcggc ttggggccac cctgctgtgc ctgctgctgg cggcggcggt ccccacggcc      60
cccgcgcccg ctccgacggc gacctcggct ccagtcaagc ccggcccggc tctcagctac     120
ccgcaggagg aggccaccct caatgagatg ttccgcgagg ttgaggaact gatggaggac     180
acgcagcaca aattgcgcag cgcggtggaa gagatggagg cagaagaagc tgctgctaaa     240
gcatcatcag aagtgaacct ggcaaactta cctcccagct atcacaatga gaccaacaca     300
gacacgaagg ttggaaataa taccatccat gtgcaccgag aaattcacaa gataaccaac     360
aaccagactg gacaaatggt cttttcagag acagttatca catctgtggg agacgaagaa     420
ggcagaagga gccacgagtg catcatcgac gaggactgtg ggcccagcat gtactgccag     480
tttgccagct ccagtacacc tgccagccac tgccggggcc agaggatgct ctgcacccgg     540
gacagtgagt gctgtggaga ccagctgtgt gtctggggtc actgcaccaa aatggccacc     600
aggggcagca atgggaccat ctgtgacaac cagagggact gccagccggg gctgtgctgt     660
gccttccaga gaggcctgct gttccctgtg tgcacacccc tgcccgtgga gggcgagctt     720
tgccatgacc ccgccagccg gcttctggac ctcatcacct gggagctaga gcctgatgga     780
gccttggacc gatgcccttg tgccagtggc ctcctctgcc agccccacag ccacagcctg     840
gtgtatgtgt gcaagccgac cttcgtgggg agcgtgacca agatggggga gatcctgctg     900
cccagagagg tccccgatga gtatgaagtt ggcagcttca tggaggaggt cgccaggag      960
ctggaggacc tggagaggag cctgactgaa gagatggcgc tggggagcc tgcggctgcc    1020
gccgctgcac tgctgggagg ggaagagatt tag                                1053
```

<210> SEQ ID NO 3
<211> LENGTH: 20
<212> TYPE: DNA
<213> ORGANISM: Artificial Sequence
<220> FEATURE:

<223> OTHER INFORMATION: Forward Primer

<400> SEQUENCE: 3
tgaggcagtg gctacacaag         20

<210> SEQ ID NO 4
<211> LENGTH: 20
<212> TYPE: DNA
<213> ORGANISM: Artificial Sequence
<220> FEATURE:
<223> OTHER INFORMATION: Reverse Primer

<400> SEQUENCE: 4
gctggtatgg ggttgagaga         20

<210> SEQ ID NO 5
<211> LENGTH: 20
<212> TYPE: DNA
<213> ORGANISM: Artificial Sequence
<220> FEATURE:
<223> OTHER INFORMATION: GAPDH forward

<400> SEQUENCE: 5
acccagaaga ctgtggatgg         20

<210> SEQ ID NO 6
<211> LENGTH: 20
<212> TYPE: DNA
<213> ORGANISM: Artificial Sequence
<220> FEATURE:
<223> OTHER INFORMATION: GAPDH reverse

<400> SEQUENCE: 6
acacattggg ggtaggaaca         20

<210> SEQ ID NO 7
<211> LENGTH: 22
<212> TYPE: DNA
<213> ORGANISM: Artificial Sequence
<220> FEATURE:
<223> OTHER INFORMATION: Atrogin-1 forward

<400> SEQUENCE: 7
agagaggcag attcgcaagc gt         22

<210> SEQ ID NO 8
<211> LENGTH: 21
<212> TYPE: DNA
<213> ORGANISM: Artificial Sequence
<220> FEATURE:
<223> OTHER INFORMATION: Atrogin-1 reverse

<400> SEQUENCE: 8
tgcaaagctg cagggtgacc c         21

<210> SEQ ID NO 9
<211> LENGTH: 29
<212> TYPE: DNA
<213> ORGANISM: Artificial Sequence
<220> FEATURE:
<223> OTHER INFORMATION: primer-F

<400> SEQUENCE: 9
ggggtaccat ggactacaaa gaccatgac         29

```
<210> SEQ ID NO 10
<211> LENGTH: 29
<212> TYPE: DNA
<213> ORGANISM: Artificial Sequence
<220> FEATURE:
<223> OTHER INFORMATION: primer-R

<400> SEQUENCE: 10
gctctagact aaatctcctc ctctccgcc                                    29
```

UNITED STATES PATENT AND TRADEMARK OFFICE
CERTIFICATE OF CORRECTION

| | |
|---|---|
| PATENT NO. | : 11,340,221 B2 |
| APPLICATION NO. | : 15/569981 |
| DATED | : May 24, 2022 |
| INVENTOR(S) | : Ping Hu et al. |

It is certified that error appears in the above-identified patent and that said Letters Patent is hereby corrected as shown below:

On the Title Page

Item (73) Assignee, change "Shanghai Institutes for Biological Sciences, Chinese Academy of Sciences" to --Center for Excellence in Molecular Cell Science, Chinese Academy of Sciences--

Signed and Sealed this
Fourteenth Day of February, 2023

Katherine Kelly Vidal
*Director of the United States Patent and Trademark Office*